US00PP34475P2

(12) United States Plant Patent
Smit

(10) Patent No.: US PP34,475 P2
(45) Date of Patent: Aug. 2, 2022

(54) ***PEPEROMIA* PLANT NAMED 'EC-PEPE-2105'**

(50) Latin Name: *Peperomia obtusifolia*
Varietal Denomination: EC-PEPE-2105

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/677,660

(22) Filed: Feb. 22, 2022

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct cultivar of *Peperomia* plant named 'EC-PEPE-2105' is disclosed, characterized by very upright, compact habits, and good branching. Plants have red-brown colored stems, and glossy green leaves. The new variety is a *Peperomia*, typically used as an ornamental plant.

3 Drawing Sheets

Latin name of the genus and species: *Peperomia obtusifolia.*

Variety denomination: 'EC-PEPE-2105'.

BACKGROUND OF THE INVENTION

The new cultivar is a product of a planned breeding program to produce distinct and better performing *Peperomia* varieties. The new variety was selected as a seedling resulting from the crossing of *Peperomia obtusifolia* '#1402', and '#1405', two unpatented varieties from the inventor's breeding line. The crossing was made by the inventor, Obed J. Smit, a citizen of the Netherlands in 2016. 'EC-PEPE-2105' was selected by the inventor in 2017 at a commercial greenhouse in Sappemeer, the Netherlands.

Asexual reproduction of the new cultivar 'EC-PEPE-2105' by terminal cuttings was first performed in Sappemeer, the Netherlands at a commercial greenhouse in September 2017, and has shown that the unique features of this cultivar are stable and reproduced true to type through successive generations.

SUMMARY OF THE INVENTION

The cultivar 'EC-PEPE-2105' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2105'. These characteristics in combination distinguish 'EC-PEPE-2105' as a new and distinct *Peperomia* cultivar:

1. Glossy green leaves.
2. Red-brown colored stems with very short internodes.
3. Very compact, upright plant habit.
4. Good branching, new side-shoots develop naturally from the axils.

PARENT COMPARISON

Plants of the new cultivar 'EC-PEPE-2105' are similar to plants of the female parent, *Peperomia obtusifolia* '#1402' in most horticultural characteristics, however, plants of the new cultivar 'EC-PEPE-2105' differ from in the following characteristics:

1. Stems of the new variety are red-brown colored, while stems of the seed parent are brown.
2. Stems of the new variety are thicker than stems of the seed parent.
3. Leaves of the new variety are glossy green, while leaves of the seed parent are light green.
4. Leaves of the new variety are smaller than leaves of the seed parent.
5. Internodes of the new variety are shorter and more compact than internodes of the seed parent.

Plants of the new cultivar 'EC-PEPE-2105' are similar to plants of the male parent, *Peperomia obtusifolia* '#1405' in most horticultural characteristics, however, plants of the new cultivar 'EC-PEPE-2105' differ in the following characteristics:

1. Stems of the new variety are thinner than stems of the pollen parent.
2. Leaves of the new variety are glossy green, while leaves of the pollen parent are dark green.
3. Internodes of the new variety are shorter and more compact than internodes of the pollen parent.

COMMERCIAL COMPARISON

Plants of the new cultivar 'EC-PEPE-2105' are similar to plants of the commercial variety *Peperomia obtusifolia* 'EC-PEPE-1806', U.S. Plant Pat. No. 31,313. However, plants of the new cultivar differ in the following characteristics:

1. Stems of the new variety are red-brown colored, while stems of this comparator are red.
2. Leaves of the new variety are glossy green, while leaves of this comparator are light green.
3. Leaves of the new variety are smooth with veins that are barely visible, while leaves of this comparator have more visible, deeper lying veins.
4. Internodes of the new variety are shorter and more compact than internodes of this comparator.

Plants of the new cultivar 'EC-PEPE-2105' are similar to plants of *Peperomia obtusifolia* 'Obtipan', U.S. Plant Pat. No. 29,598. However, plants of the new cultivar differ in the following characteristics:

1. Stems of the new variety are red-brown colored, while stems of this comparator are brown.
2. Leaves of the new variety are glossy green, while leaves of this comparator are dark green.
3. Internodes of the new variety are shorter and more compact than internodes of this comparator.

BRIEF DESCRIPTION OF THE PHOTOGRAPHS

The accompanying photograph in FIG. 1 illustrates in full color a typical blooming plant of 'EC-PEPE-2105' grown in a greenhouse. The plant is approximately 25 weeks of age.

Figure 1:
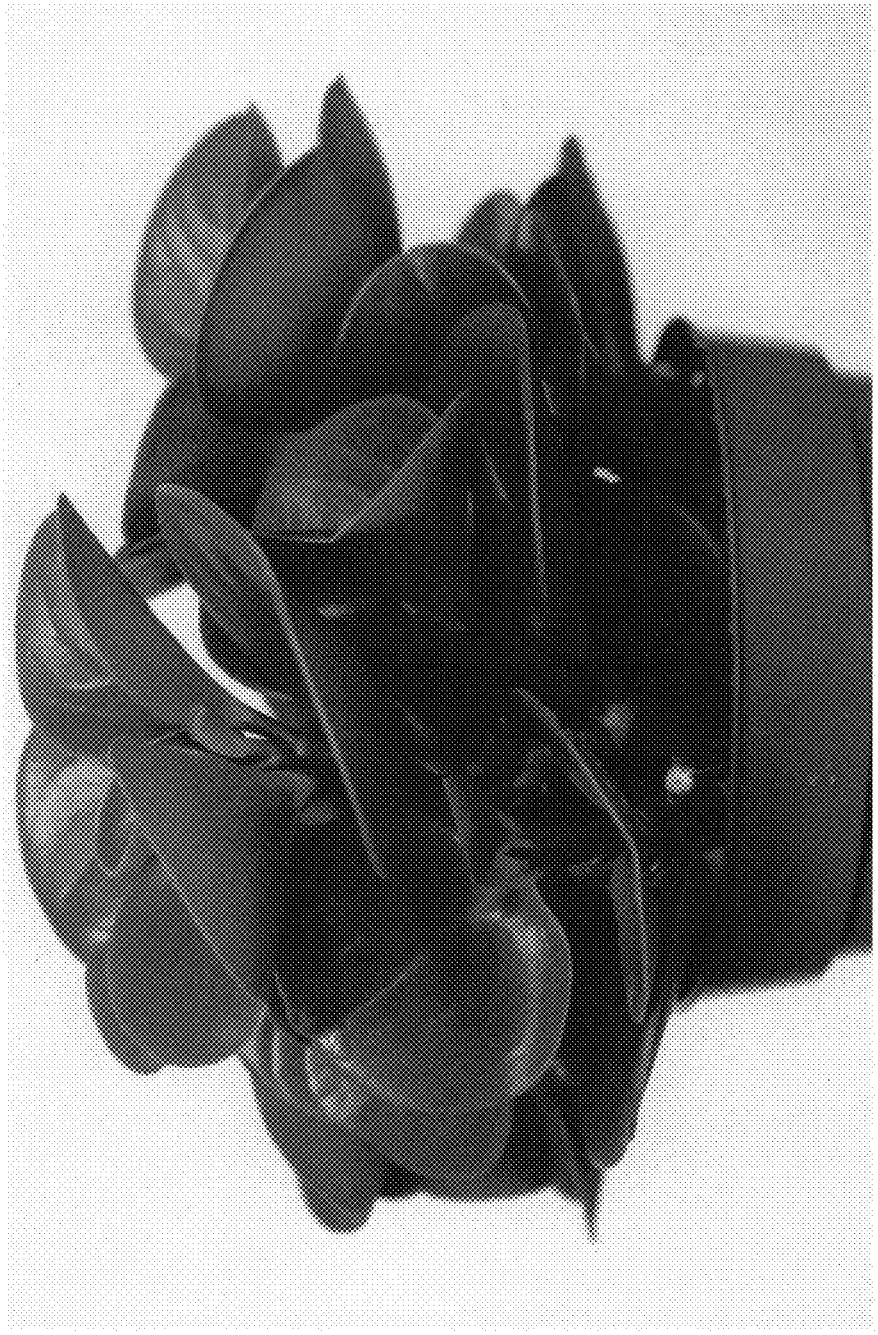
Figure 2:
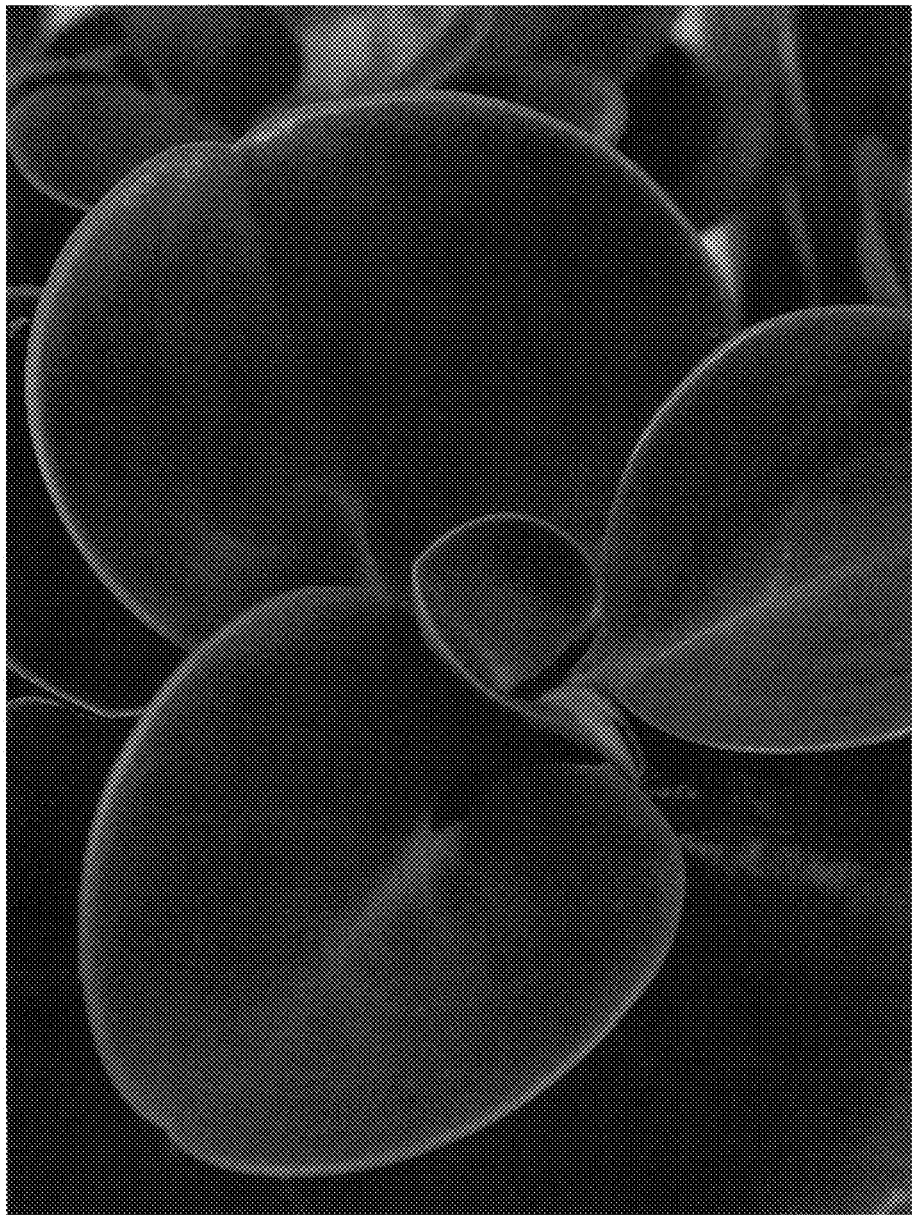
FIG. 2 illustrates a close up of the foliage.
Figure 3:
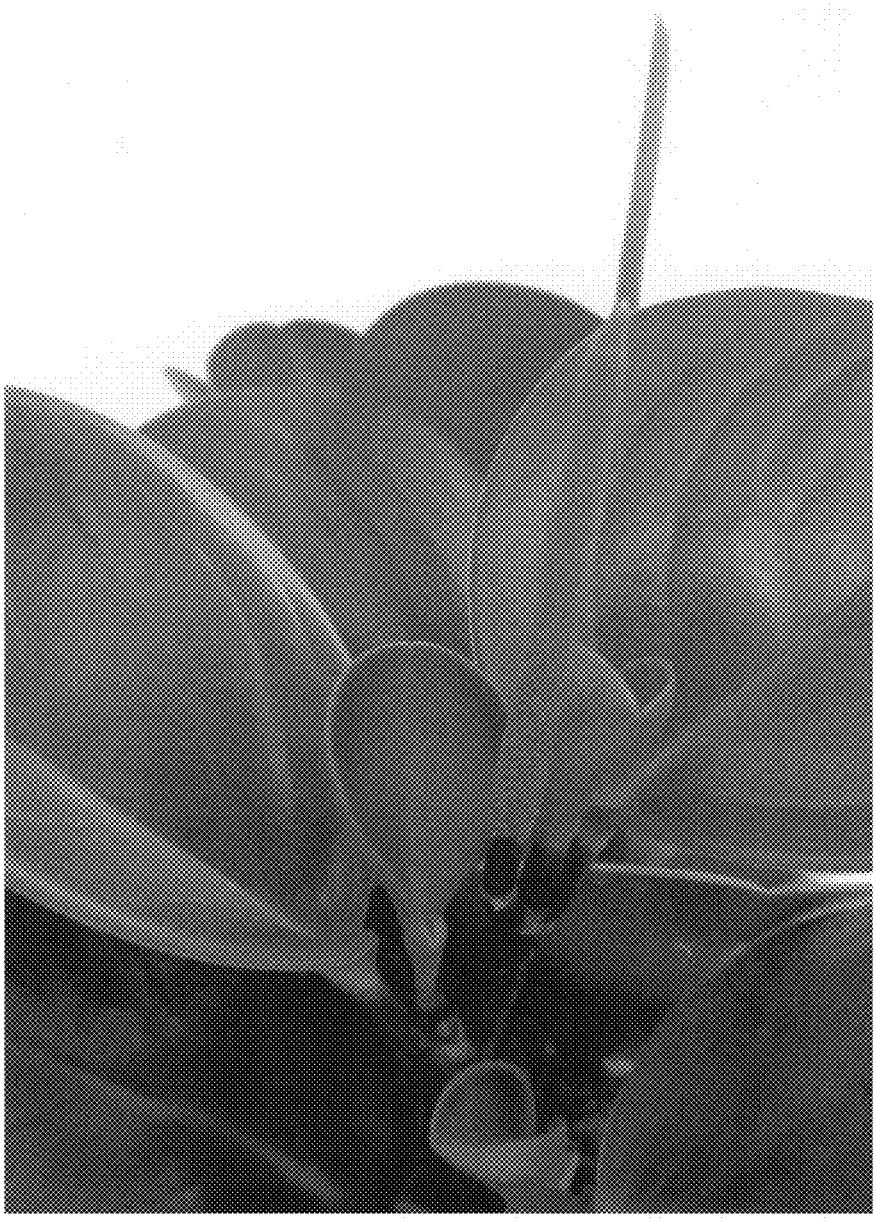
FIG. 3 illustrates typical inflorescences.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2105' plants at 10 weeks of age, grown in a greenhouse in Sappemeer, the Netherlands during December. The growing temperature ranged from 18° C. to 20° C. at night to 20° C. to 23° C. during the day. Measurements and numerical values represent averages of typical flowering types.

Botanical classification: *Peperomia obtusifolia* 'EC-PEPE-2105'.

PROPAGATION

Time to initiate roots: About 7 days at 20° C. in summer, 10 days at 20° C. in winter.

Time to produce rooted cutting: About 25 days at 20° C. in summer.

Description of roots: Fibrous, fine, moderately dense, freely branching. White in color, not accurately measured with R.H.S. chart.

PLANT

Plant type: Perennial potted plant.
Plant shape: Obovate.
Growth habit: Basal and lateral branching.
Plant spread: Approximately 12.4 cm.
Height: 11.9 cm to top of foliar plane.
Growth rate: Low to moderate.
Plant vigor: Moderate.
Age of plant described: Approximately 6 months.
Branching habit: Basal and lateral branching.
Pinching: Pinching not required.
Number of primary (main) branches per plant: Average 3.
Number of secondary (lateral) branches per plant: Average 3.
Main branches:
*Length*.—Average: 3 cm.
*Diameter*.—Average: 0.5 cm.
Internode length: Average: 1.2 cm.
Appearance and shape: Succulent, thick and rounded.
Luster: Glossy.
Aspect/angle from vertical: Average angle: 25°.
Strength: Moderately strong.
Color:
*Developing*.—RHS Yellow-Green 146D; heavily, finely mottled Greyed-Red 182A.
*Mature*.—RHS Yellow-Green 146D and lighter; heavily, finely mottled Greyed-Purple 183C and 183D.
*At internodes*.—RHS Yellow-Green 145A; finely mottled Greyed-Red 182A.
Pubescence: None.
Plant fragrance: None.

FOLIAGE

Leaf:
*Arrangement*.—Alternate, single.
*Quantity*.—Average 3 per lateral branch.
*Average length*.—3.3 cm.
*Average width*.—2.4 cm.
*Shape of blade*.—Reniform to near orbicular.
*Aspect*.—Moderately convex.
*Apex*.—Broad retuse.
*Base*.—Short attenuate.
*Margin*.—Entire.
*Texture of top surface*.—Glabrous, smooth, leathery.
*Texture of bottom surface*.—Glabrous, smooth, leathery.
*Pubescence*.—None.
*Luster, upper side*.—Glossy.
*Luster, under side*.—Moderately glossy.
*Color*.—Young foliage upper side: RHS Green 137A, narrowly margined 143C. Young foliage under side: RHS Yellow-Green 144B. Mature foliage upper side: RHS Green NN137A. Mature foliage under side: Blend of RHS Yellow-Green 144A and 146B.
*Venation*.—Pattern: Pinnate. Venation color upper side: RHS Yellow-Green 144B, fading lighter at base to 145A. Venation color under side: RHS Yellow-Green 146A.
*Petiole*.—Average Length: 1 cm. Diameter: Flattened, diameter at widest 0.4 cm; 0.3 cm at narrowest. Texture: Glabrous, smooth. Luster: Both sides moderately glossy. Strength: Medium. Color, upper side: RHS Greyed-Purple 183B, finely, irregularly striped and flushed Yellow-Green 146C. Color, under side: RHS Greyed-Purple 183A, slightly finely, irregularly striped and flushed Yellow-Green 146D.
*Other leaf characteristics*.—On the main vein on under side of each leaf, one or two glands are present: circular-shaped, average diameter 1 mm, colored RHS Brown 200C and 200D.

FLOWER

Flowers not observed during data collection for filing.

OTHER CHARACTERISTICS

Seeds and fruits: None observed to date.

Disease/pest resistance: No increased nor decreased resistance nor susceptibility to normal diseases and pests of *Peperomia* has been observed.

Temperature tolerance: Tolerates temperatures up to 40° C. Hardy to USDA zones 10 to 12.

What is claimed is:

1. A new and distinct cultivar of *Peperomia* plant named 'EC-PEPE-2105' as herein illustrated and described.

* * * * *